US009283234B2

(12) United States Patent
Podolski

(10) Patent No.: US 9,283,234 B2
(45) Date of Patent: *Mar. 15, 2016

(54) COMPOSITIONS AND METHODS FOR SUPPRESSING ENDOMETRIAL PROLIFERATION

(75) Inventor: Joseph S. Podolski, The Woodlands, TX (US)

(73) Assignee: REPROS THERAPEUTICS INC., The Woodlands, TX (US)

( * ) Notice: Subject to any disclaimer, the term of this patent is extended or adjusted under 35 U.S.C. 154(b) by 808 days.

This patent is subject to a terminal disclaimer.

(21) Appl. No.: 12/446,567

(22) PCT Filed: Oct. 24, 2007

(86) PCT No.: PCT/US2007/082432
§ 371 (c)(1),
(2), (4) Date: Apr. 27, 2010

(87) PCT Pub. No.: WO2008/067086
PCT Pub. Date: Jun. 5, 2008

(65) Prior Publication Data
US 2010/0216756 A1 Aug. 26, 2010

Related U.S. Application Data

(60) Provisional application No. 60/862,632, filed on Oct. 24, 2006, provisional application No. 60/885,348, filed on Jan. 17, 2007.

(51) Int. Cl.
*A61K 31/56* (2006.01)
*A61K 31/573* (2006.01)

(52) U.S. Cl.
CPC ............... *A61K 31/573* (2013.01); *A61K 31/56* (2013.01)

(58) Field of Classification Search
USPC ........................................................ 514/179
See application file for complete search history.

(56) References Cited

U.S. PATENT DOCUMENTS

| 4,038,389 | A | * | 7/1977 | Lamb ............................. 514/178 |
| 5,521,166 | A | | 5/1996 | Grubb |
| 5,681,817 | A | | 10/1997 | Hodgen et al. |
| 5,780,050 | A | * | 7/1998 | Jain et al. ......................... 424/449 |
| 6,689,768 | B2 | * | 2/2004 | Oettel et al. ..................... 514/182 |
| 2002/0058035 | A1 | * | 5/2002 | Garnick et al. ............. 424/145.1 |

FOREIGN PATENT DOCUMENTS

| WO | 94/18983 | | 9/1994 |
| WO | 95/20972 | | 8/1995 |
| WO | 97/41145 | | 11/1997 |
| WO | 99/45022 | A1 | 9/1999 |
| WO | 01/47945 | A1 | 4/2001 |
| WO | WO01/64236 | * | 9/2001 |
| WO | 2006/010097 | A2 | 1/2006 |
| WO | 01/74840 | A2 | 10/2011 |

OTHER PUBLICATIONS

Attardi et al. (CDB-4124 and its putative monodemethylated metabolite, CDB-4453, are potent antiprogestins with reducedantiglucocorticoid activity: in vitro comparison to mifepristone and CDB-2914. Molecular and Cellular Endocrinology 188 (2002) 111-123).*
Gemzell-Danielsson et al. (Effect of low weekly doses of mifepristone on ovarian function and endometrial development. Hum. Reprod. (2000) 15 (5): 1092-1099).*
International Search Report of PCT/US2007/82432 dated Sep. 9, 2008.
International Preliminary Report on Patentability of PCT/US2007/082432 dated May 7, 2009.
Danielsson, K.G., et al., Human Reproduction, vol. 132, No. 1, pp. 124-131 (1997).
Greb, R.R., et al., Human Reproduction, vol. 14, No. 1, pp. 198-206 (1999).
Written Opinion dated Apr. 7, 2010 from Australian Patent Office for Singapore Patent Applic. No. 200902374-8.
Kettel, L., et al., Preliminary Report on the Treatment of Endometriosis with Low-Dose Mifepristone (RU 486), Am. J. Obstet. Gynecol., vol. 178, pp. 1151-1156 (Jun. 1998).
Donnez, Jacques, M.D., et al., "Long-Term Treatment of Uterine Fibroids with Ulipristal Acetate," Seminal Contributions, Fertility and STerility, vol. 101, No. 6, pp. 1565-1573 (Jun. 2014).
Repros Therapeutics Inc. Announces That Proellex Administered to Patients as Cyclic Therapy to Treat the Symptoms of Uterine Fibroids for Up to 30 Months Shows No Adverse Effects on the Endometrium, Drug Information Online—Drugs.com, pp. 1-2, Jul. 2008.
Spitz, Irving M.,"Clinical Utility of Progesterone Receptor Moulators and Their Effect on the Endometrium," Current Opinion in Obstetrics & Gynecology, vol. 21, No. 4, pp. 318-324 (Aug. 2009).
Chabbert-Buffet, N., et al., "Effects of the Progesterone Receptor Modulator VA2914 in a Continuous Low Dose on the Hypothalamic-Pituitary-Ovarian Axis and Endometrium in Normal Women: A Prospective, Randomized, Placebo-Controlled Trial," Journal of Clinical Endocrin. & Metabol., vol. 92, No. 9, pp. 3582-3589 (2007).
Colca, J., "Discontinued drug in 2007: Renal, Endocrine and Metabolic drugs," Expert Opinion on Investigational Drugs, vol. 17, No. 11, pp. 1641-1650 (2008).

(Continued)

*Primary Examiner* — Layla Soroush
(74) *Attorney, Agent, or Firm* — Morgan Lewis & Bockius LLP

(57) ABSTRACT

The subject matter of the instant invention is pertinent to the field of hormone therapy. More specifically, the subject matter of the instant invention concerns methods of treating estrogen-dependent conditions such as endometrial hyperplasia and endometrial cancer in a female undergoing estrogen and/or selective estrogen receptor modulator (SERM) therapy. The instant invention is also relevant to the suppression of endometrial proliferation. The instant invention is also relevant to the treatment of pain associated with endometriosis. The compositions for practicing the methods, comprising progesterone antagonists are also disclosed. Embodiments of the instant invention also disclose methods for identifying new selective progesterone receptor modulators for practicing disclosed methods of treatment.

7 Claims, 2 Drawing Sheets

(56) References Cited

OTHER PUBLICATIONS

Cullen, A., "Schering, TAP Halt Trial of Drug for Uterine Growth (Update5)," Bloomberg, 2 pages, Oct. 12, 2005.

Extended European Search Report, of EP 07871232.0 dated Aug. 16, 2011.

Murphy, A., et al., "Endometrial Effects of Long-Term Low-Dose Administration of RU486," Fertil Steril., vol. 63, No. 4, pp. 761-766 (1995) Abstract.

Mutter, G. L., et al., "The Spectrum of Endometrial Pathology Induced by Progesterone Receptor Modulators," Modern Pathology, pp. 1-8 (2008).

Wang, X., et al., "Clinical Study on the Treatment of Adenomyosis with Mifepristone," Shanxi Clinical Medicine J., vol. 10, No. 9, pp. 660-661 (2001) with English translation.

Blithe, Diana., et al., "Development of the Selective Progesterone Receptor Modulator CDB-2914 for Clinilcal Indications," Steroids, vol. 68, Issues 10-13, pp. 1013-1017 (Nov. 2003).

Chwalisz, K., et al., "Antiproliferative Effects of Progesterone Antagonists and Progesterone Receptor Modulators on the Endometrium," Steroids, vol. 65, pp. 741-751 (Oct.-Nov. 2000).

Eisenberg, Ester, MD, "Endometriosis" The Merck Manuals Online Library, at http://www.merckmanuals.com/professional/gynecology-and-obstetrics/endometriosis/endometriosis, revised Feb. 2013.

Nelson, A., "Extended-Cycle Oral Contraception: A New Option for Routine Use," Treatments in Endocrinology, vol. 4, No. 3, pp. 139-145 (Jun. 2005).

Wiegratz, E., et al., "Long-Cycle Treatment with Oral Contraceptives," Drugs, vol. 64, No. 21, pp. 2447-2462 (Nov. 2004).

\* cited by examiner

COMPOSITIONS AND METHODS FOR SUPPRESSING ENDOMETRIAL PROLIFERATION

CROSS-REFERENCE TO RELATED APPLICATIONS

The present application is the National Stage of International Application Number PCT/US2007/082432, filed Oct. 24, 2007, which claims the benefit of U.S. Provisional Patent Application No. 60/862,632, filed Oct. 24, 2006, and U.S. Provisional Patent Application No. 60/885,348, filed Jan. 17, 2007, the contents of each of which is incorporated herein by reference in its entirety.

FIELD OF THE INVENTION

The present invention relates to compositions and methods for the suppressing endometrial proliferation. More specifically, the present invention relates to compositions comprising one or more progesterone antagonists for suppressing endometrial proliferation.

BACKGROUND OF THE INVENTION

Estrogens are a group of hormones essential for a variety of physiologic processes including the development of the uterus and breasts, the maintenance of bone density, and cardiovascular protection through its positive effect on lipid profiles. The effects of estrogen are mediated through its binding to estrogen receptors in the nucleus. According to the classic model, unoccupied estrogen receptor in the nucleus, upon binding estrogen, acquires the ability to interact with DNA sequences within the promoters of estrogen-responsive genes. The DNA-bound estrogen receptor modulates the transcription of these genes, either positively or negatively.

Estrogen is known to have a hyperproliferative effect on breast and uterine tissue. Administration of unopposed estrogen to menopausal women, for example, has been demonstrated to lead to both endometrial hyperplasia and endometrial cancer. In contrast, progesterone potently counteracts estrogen-dependent endometrial proliferation and cancer development. Therefore, to counteract the effects of unopposed estrogen, progestin is commonly prescribed as part of a hormone replacement therapy (HRT). However, a large clinical study from the Women's Health Initiative recently determined that the combination of conjugated estrogen and medroxyprogesterone acetate increased the risk of developing cardiovascular disease, stroke, pulmonary embolism and breast cancer. Additionally, experimental data in macaques made surgically menopausal has shown that a regimen of combined estrogen and progesterone led to higher levels of breast proliferation and hyperplasia then estrogen alone. Coadministration of progestin has also been associated with break-through bleeding, further limiting its suitability as an agent for countering the hyperproliferative effects of estrogen.

Many compounds are known in the art which affect estrogen-dependent activation of the estrogen receptor. Depending on a variety of factors these compounds may be entirely estrogenic, in that they mimic estrogen, entirely antiestrogenic, in that they block the effects of estrogen, or they may fall somewhere in-between. Compounds which exhibit mixed estrogenic and antiestrogenic properties are termed selective estrogen receptor modulators (SERMs). SERMs exert their estrogenic or antiestrogenic effects in a tissue-specific manner. The mechanism underlying this tissue-specificity is not clear, but may involve, inter alia, the recruitment of corepressor and coactivator proteins whose relative expression levels vary among tissue types and tissue-specific expression of estrogen receptor isoforms α and β. Estrogen receptor α is an activator whereas estrogen receptor β can inhibit estrogen receptor α activity by forming a heterodimer with it.

The dual activities of SERMs provide several potential advantages to women. The estrogenic properties of SERMs may be used to treat or prevent diseases caused by estrogen deficiency such as osteoporosis, while minimizing some of the undesirable effects of estrogen. Conversely, the antiestrogenic properties of SERMs may be used to prevent or treat diseases such as breast cancer, in which estrogenic activity is undesirable. Nonetheless, endometrial hyperplasia has been associated with SERM therapy, thus limiting its usefulness.

The SERM tamoxifen, for example, has been shown to be antiestrogenic in the breast where it blocks the proliferative effects of estrogen and has consequently found favor as a treatment for certain types of breast cancer. On the other hand, tamoxifen displays estrogenic effects on bone and the uterus and has been associated with an increased incidence of endometrial hyperplasia and endometrial cancer, limiting it's usefulness as an antiestrogen.

A preliminary study in primates appeared to indicate that antiprogestins possess antiproliferative effects on the endometrium. However, there is concern that long-term treatment with antiprogestins could result in endometrial hyperplasia due to the action of unopposed estrogen. Several recent investigations in adult women have revealed a thickening of the endometrium during long-term treatment with high doses of antiprogestins, presumably a consequence of unopposed estrogen activity, which does not appear to occur with low doses.

There remains a need for a treatment regimen suitable for long-term administration which opposes the proliferative effects of estrogen while maintaining the beneficial effects of estrogen on the body.

SUMMARY OF THE INVENTION

The instant invention provides methods for suppressing endometrial proliferation comprising administering to a patient in need thereof, an amount of a progesterone antagonist effective to suppress proliferation in endometrial tissue. The patient in need thereof may be a female with endometriosis. The progesterone antagonist may be a pure antiprogestin or a selective progesterone receptor modulator (SPRM). In a preferred embodiment, the progesterone antagonist has low affinity for glucocorticoid receptor. In another preferred embodiment, administration of the progesterone antagonist to a female reduces luteal phase progesterone levels in the female. In yet another preferred embodiment, administration of the progesterone antagonist to a female does not substantially lower estrogen levels in the female.

In yet another aspect, the instant invention provides methods of using progesterone antagonists in estrogen and SERM therapies to prevent an estrogen-dependent condition. More specifically, the instant invention employs progesterone antagonists at dosages sufficient to suppress endometrial proliferation in females undergoing treatment regimens comprising the administration of an estrogen or SERM. For example, the patient may be a menopausal or post-menopausal female undergoing hormone replacement therapy. In yet another aspect, the invention provides methods for preventing the development of endometrial hyperplasia and/or endometrial cancer using progesterone antagonists in estrogen and SERM therapies. The progesterone antagonist may be an antiprogestin or a selective progesterone receptor modulator (SPRM) so long as the progesterone antagonist is used in an amount effective to suppress endometrial proliferation.

In yet another aspect, the instant invention provides methods of using progesterone antagonists in the treatment of pain associated with endometriosis. The progesterone antagonists may be used for long-term treatment of pain associated with endometriosis.

DETAILED DESCRIPTION OF THE INVENTION

Figure 1:
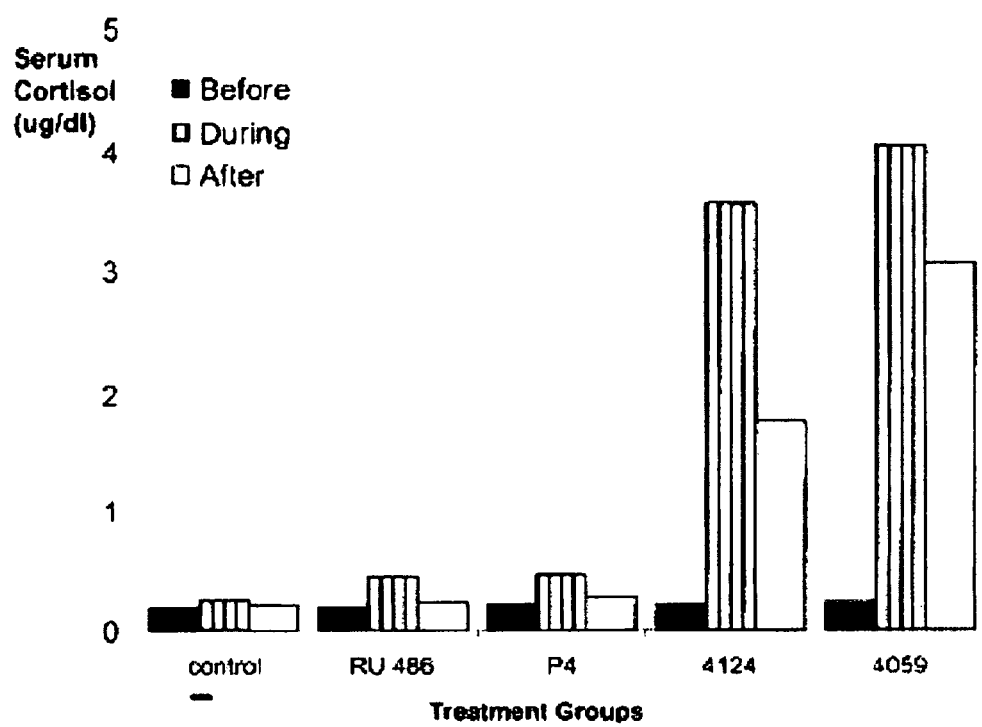
FIG. 1 is a graph depicting the effect of selective progesterone receptor modulators on serum cortisol in rats.

The term "effective dosage" means an amount of the composition's active component sufficient to achieve the desired effect which may be, e.g., suppression of endometrial proliferation or treatment of pain associated with endometriosis.

The term "selective progesterone receptor modulators" means compounds that affect functions of progesterone receptor in a tissue-specific manner. The compounds act as progesterone receptor antagonists in some tissues (for example, in the uterus) and as progesterone receptor agonists in other tissues.

The terms "treat" or "treatment" refer to both therapeutic treatment and prophylactic or preventative measures, wherein the object is to prevent or slow down (lessen) an undesired physiological change or disorder. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "progesterone agonist" means a compound that binds to a progesterone receptor and mimics the action of the natural hormone.

The term "progesterone antagonist" means a compound that binds to a progesterone receptor and inhibits the effect of progesterone.

The term "suppress" or "suppresses" or "suppressing" used herein in reference to proliferation of endometrial tissue means that mitotic proliferation of endometrial tissue is suppressed upon administration of a progesterone antagonist relative to untreated endometrial tissue under identical conditions and is to be distinguished from cell death via, e.g., apoptosis. The activity of a progesterone antagonist in suppressing endometrial mitotic proliferation may be tested, e.g., in a uterine cell line by, e.g., comparing the incorporation of bromodeoxyuridine (BrdU) in cells treated with a progesterone antagonist to control (untreated) cells.

The term "not substantially reduced" as used herein in reference to hormone levels in a female means that hormone levels are maintained within the normal range during administration of compositions of the invention. Thus, it is considered that some reduction in a hormone level may occur so long as the hormone level is maintained within the normal range.

The term "not substantially increased" as used herein in reference to hormone levels in a female means that hormone levels are maintained within the normal range during administration of compositions of the invention. Thus, it is considered that some elevation in a hormone level may occur so long the hormone level is maintained within the normal range.

The present invention relates to the use of progesterone antagonists at doses effective to suppress endometrial proliferation. The methods arise from the unexpected finding that certain progesterone antagonists exhibit an inverse dose dependent effect on endometrial proliferation, while maintaining estrogen levels within the normal range. Specifically, it has been found that chronic administration of a high dosage of the antiprogestin/SPRM CDB-4124 suppresses endometrial proliferation while lower doses fail to suppress endometrial proliferation and even tend to promote endometrial proliferation, despite similar levels of estrogen observed at high and low dosages. This is particularly surprising in view of the inability of the antiprogestin/SPRM RU 486 to suppress endometrial proliferation at a high dosage, demonstrated below, and several recent reports that chronic administration of high doses of antiprogestins promotes endometrial proliferation, presumably due to the effects of unopposed estrogen. The present invention also demonstrates that progesterone antagonists are unexpectedly useful in treating pain associated with endometriosis.

The suppression of endometrial proliferation during a treatment regimen comprising the daily administration of an effective amount of a progesterone antagonist over a six month period, described below, demonstrates the usefulness of such progesterone antagonists where chronic/long-term administration is desired. In this regard, methods of the invention may comprise administering a composition comprising an amount of a progesterone antagonist sufficient for suppressing endometrial proliferation for an administration period of least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The composition may also be administered for an administration period of least 1, 2, 3, 4, 5, 6, 7, 8, 9, 10, 11, 12 or more months. The composition may also be administered for an administration period of at least 1, 2, 3, 4, 5, 6, 7, 8, 9, 10 or more years. During the administration period, the composition may be administered daily or periodically such as every other day, every other month, and the like. The composition may also be administered intermittently. For example, the composition may be administered for an administration period of 1, 2, 3, 4, 5 or more months, followed by a period of discontinuance, followed by an administration period of 1, 2, 3, 4, 5 or more months, and so on.

By "intermittent administration" it is meant a period of administration of a therapeutically effective dose of progesterone antagonist, followed by a time period of discontinuance, which is then followed by another administration period and so forth.

By "period of discontinuance" or "discontinuance period" it is meant a discontinuing of the daily, weekly, monthly or therebetween administration of progesterone antagonist. The time period of discontinuance may be longer or shorter than the administration period but is always longer than the dosing interval during the administration period. For example, where the administration period comprises daily, weekly, or monthly dosing, the discontinuance period is at least 2 days, at least 8 days or at least 32 days, respectively. Thus, the discontinuance period may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more days.

In one embodiment, the composition is administered intermittently such that the subject undergoes menses during at least one discontinuance period. This approach is expected to avoid the adverse effects associated with a thickened or stagnant endometrium that may accompany extended treatment with progesterone antagonists, such as spotting, breakthrough bleeding, endometrial hyperproliferation or endometrial cancer. At least one, and preferably every discontinuance period is of sufficient length for the subject to experience menstruation. More preferably, the subject experiences menstruation during every discontinuance period. In a particularly preferred embodiment, the composition is administered daily for an administration period of four months, followed by a discontinuance period during which the subject experiences menstruation, followed by another administration period of four months and so on.

Optionally, a gonadtropin-releasing hormone (GnRH) agonist or antagonist may administered during the discontinuance period to hasten the shedding and refreshing of the endometrium. Non-limiting examples of GnRH agonists include nafarelin, buserelin, leuprorelin, triptorelin, goserelin, [DLys$^6$]GnRH, [DAla$^6$]GnRH and the like. Non-limiting examples of GnRH antagonists include histrelin, abarelix and those found in U.S. Pat. Nos. 4,409,208, 4,547,370, 4,565,804, 4,569,927 and 4,619,914, incorporated herein in by reference in their entirety.

Optionally, a progestin may be administered during the discontinuance period in order to obtain a normal menses in the patient. Administration of a progestin preferably results in a progesterone profile that mimics the natural rise and fall of progesterone levels during menstruation. Such treatment regimens are well known in the art. Administration of a progestin during the discontinuance period may also provide opposition to the effects of estrogen in addition to that received by administration of the progesterone antagonist and therefore may help treat estrogen-dependent conditions such as thickening of the endometrium. Non-limiting examples of progestins include medrogestone, medroxyprogesterone, megestrol, norethindrone, progesterone, hydroxyprogesterone, acetoxypregnenolone, allylestrenol, cyproterone, desogestrel, dimethisterone, ethisterone, ethynodiol diacetate, gestadene, lynestrenol and the like.

In one embodiment, a female patient with endometriosis is administered a composition comprising a progesterone antagonist in an amount effective to suppress endometrial proliferation. In a related embodiment, a composition comprising a progesterone antagonist is administered to a female with endometriosis in an amount effective to treat pain associated with endometriosis. For example, administration of the progesterone antagonist may reduce pain associated with endometrial lesions. Pain is the most prevalent and debilitating symptom of endometriosis and is the primary indication for both medical and surgical treatment of the disease. Pain may be manifested as dysmenorrheal, pelvic pain, back pain, abdominal pain, breast pain, dyspareunia and the like. Administration of the progesterone antagonist may also reduce the size of the endometrial lesions. Current regimens for the treatment of endometriosis include GnRH agonists which induce a state of pseudomenopause by inhibiting ovarian estrogen secretion and are therefore not useful for long-term administration due to loss in bone density, loss of total body calcium and other osteoporosis-like side effects. Compositions of the invention may be administered long-term with no substantial decrease in estrogen levels.

In another embodiment, the present invention provides methods of treating an estrogen-dependent condition associated with current hormone therapies which employ estrogenic compounds such as estrogens or SERMS by co-administering an amount of a progesterone antagonist effective to suppress endometrial proliferation. Estrogen-dependent conditions associated with current estrogen/SERM hormone therapies include, without limitation, endometrial hyperplasia and endometrial cancer. In this regard, the progesterone antagonist may be administered prior to, during, or subsequent to estrogens or SERMS as part of a combined hormone therapy regimen.

In yet another embodiment, the present invention provides a method of hormone replacement comprising administering to a menopausal or post-menopausal female an effective amount of a progesterone antagonist and an estrogenic compound, wherein the amount of a progesterone agonist is effective to suppress an estrogen-dependent condition. The estrogenic compound may be an estrogen or a SERM. The estrogenic compound may be administered prior to, subsequent to, or may be co-administered with, the progesterone antagonist. The estrogen-dependent condition may be, without limitation, endometrial proliferation, endometrial hyperproliferation or endometrial cancer.

In a preferred embodiment of each method of the invention, administration of the progesterone antagonist to a female does not substantially reduce estrogen levels in the female. Thus the present invention provides an advantage over current therapies for the treatment of endometriosis which often employ gonadotropin-releasing hormone (GnRH) agonists such as LUPRON (leuprolide acetate).

In another preferred embodiment of each method of the invention, administration of the progesterone antagonist to a female does not substantially increase progesterone levels in the female. More preferably, administration of the progesterone antagonist to a female reduces progesterone levels in the female, particularly luteal phase progesterone levels.

In yet another preferred embodiment of each method of the invention, the progesterone antagonist exhibits reduced affinity for the glucocorticoid receptor. More preferably, the binding affinity of the progesterone antagonist for the progesterone receptor is at least 1.5 times greater than the binding affinity of the progesterone antagonist for the glucocorticoid receptor.

Any known progesterone antagonist with characteristics of the compounds described above can be used by an artisan practicing the instant invention. Particularly useful compounds include those disclosed in U.S. Pat. No. 6,900,193, hereby incorporated by reference in its entirety, as well as those disclosed in U.S. Pat. No. 6,861,415, hereby incorporated by reference in its entirety, that are 21-substituted 19-norpregnanes with a general formula:

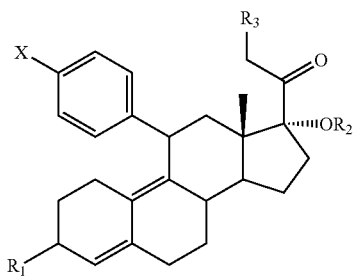

wherein:
X may be, for example alkyl, alkenyl, alkynyl, hydrogen, halo, monoalkylamino or dialkylamino, such as N,N-dimethylamino;

$R_1$ may be, for example O, NOH or NO-methyl;

$R_2$ may be, for example hydrogen or acetyl; and $R_3$ may be, for example methyloxy, formyloxy, acetoxy, acyloxy, S-alkoxy, acetyltheonyl, glycimate, vinyl ether, acethyloxymethyl, methyl carbonate, halogens, methyl, hydroxy, and ethyloxy.

The examples of 21-substituted 19-norpregnanes include, but are not limited to, the following 24 compounds disclosed below.

1. CDB-4247 (21-propio[1]nyloxy-17α-acetoxy-11β-(4 N,N-dimethylaminophenyl)-19-norpregna-4,9-diene-3,20-dione) with the following structural formula:

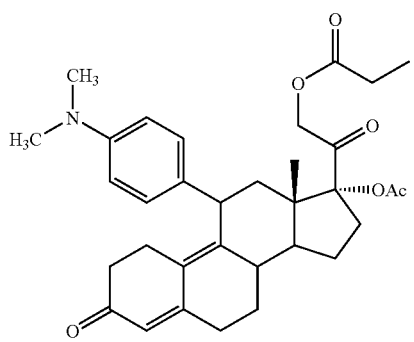

2. CDB-4361 (21-vinyl ether-17α-acetoxy-11β-(4 N,N-dimethylaminophenyl)-19-norpregna-4,9-diene-3,20-dione) with the following structural formula:

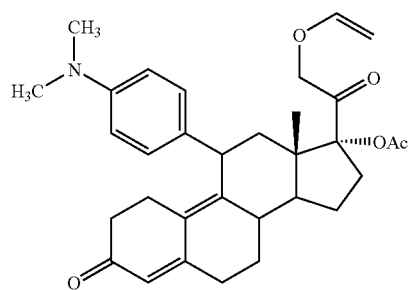

3. CDB-4059 (21-acetoxy-17α-acetoxy-1,3-(4 N,N-dimethylaminophenyl)-19-norpregna-4,9-diene-3,20-dione) with the following structural formula:

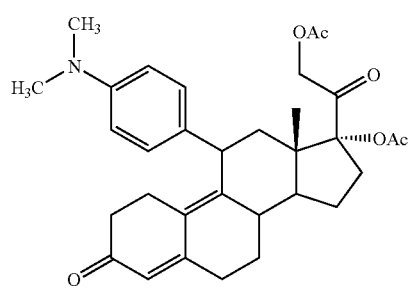

4. CDB-4124 (21-methoxy-17α-acetoxy-11β-(4 N,N-dimethylaminophenyl)-19-norpregna-4,9-diene-3,20-dione) with the following structural formula:

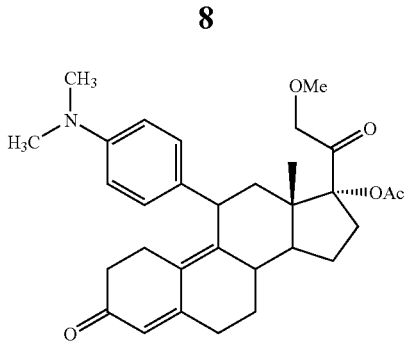

5. CDB-4031 (21-bromine-17α-acetoxy-11β-(4 N,N-dimethylaminophenyl)-19-norpregna-4,9-diene-3,20-dione) with the following structural formula:

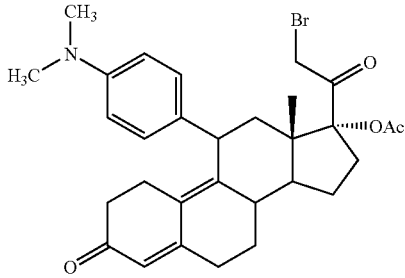

6. CDB-3876 (21-chlorine-17α-acetoxy-11β-(4 N,N-dimethylaminophenyl)-19-norpregna-4,9-diene-3,20-dione) with the following structural formula:

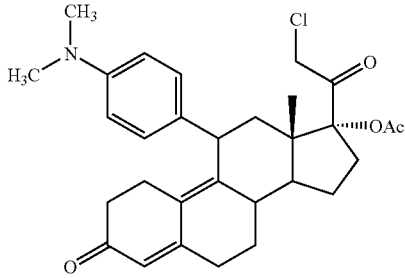

7. CDB-4058 (21-flourine-17α-acetoxy-11β-(4 N,N-dimethylaminophenyl)-19-norpregna-4,9-diene-3,20-dione) with the following structural formula:

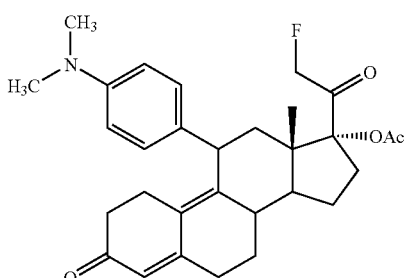

8. CDB-4030 (21-methyl-17α-acetoxy-11β-(4 N,N-dimethylaminophenyl)-19-norpregna-4,9-diene-3,20-dione) with the following structural formula:

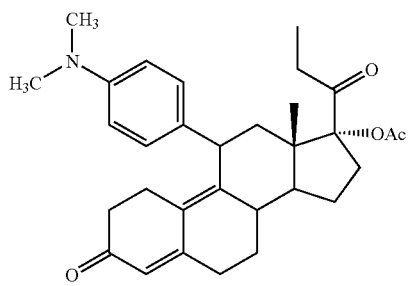

9. CDB-4152 (21-hydroxy-17α-acetoxy-11β-(4 N,N-dimethylaminophenyl)-19-norpregna-4,9-diene-3,20-dione) with the following structural formula:

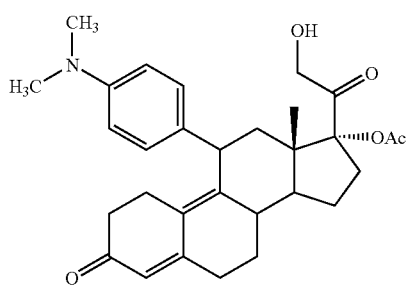

10. CDB-4167 (21-ethyloxy-17α-acetoxy-11β-(4 N,N-dimethylaminophenyl)-19-norpregna-4,9-diene-3,20-dione) with the following structural formula:

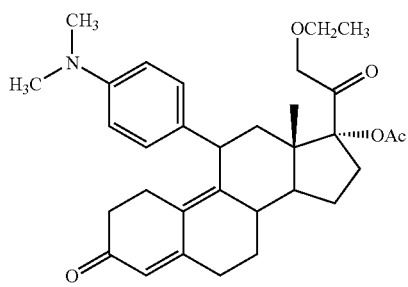

11. CDB-4101 (21-methoxythio-17α-acetoxy-11β-(4 N,N-dimethylaminophenyl)-19-norpregna-4,9-diene-3,20-dione) with the following structural formula:

12. CDB-4110 (21-acetonide-17α-acetoxy-11β-(4 N,N-dimethylaminophenyl)-19-norpregna-4,9-diene-3,20-dione) with the following structural formula:

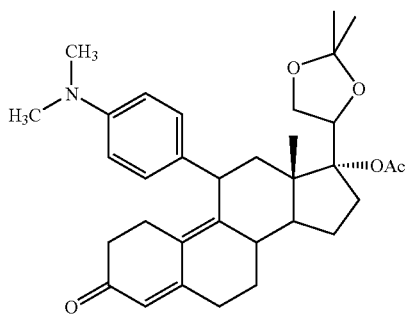

13. CDB-4111 (21-BMD-17α-acetoxy-11β-(4 N,N-dimethylaminophenyl)-19-norpregna-4,9-diene-3,20-dione) with the following structural formula:

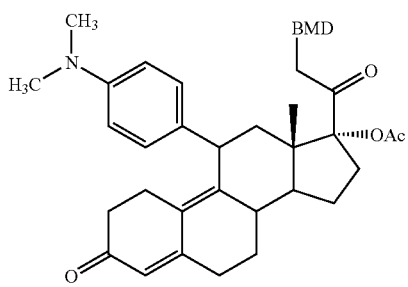

14. CDB-4125 (21-(Cyp*-hydroxy)-17α-acetoxy-11β-(4 N,N-dimethylaminophenyl)-19-norpregna-4,9-diene-3,20-dione) with the following structural formula:

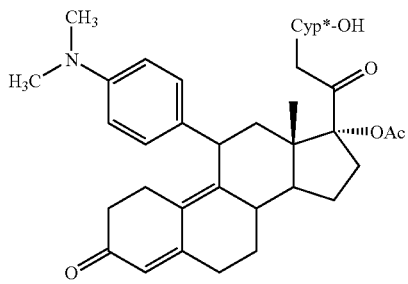

*Cyp = 3-Cyclopentylpropionyloxy-

15. CDB-4205 (3-hydroxyamino-2'-methoxy-17α-acetoxy-11β-(4 N,N-dimethylaminophenyl)-19-norpregna-4,9-diene-3,20-dione) with the following structural formula:

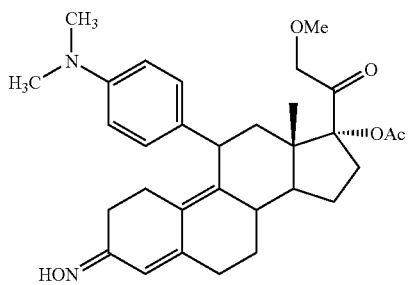

16. CDB-4206 (3-hydroxyamino-2'-acetoxy-17α-acetoxy-11β-(4 N,N-dimethylaminophenyl)-19-norpregna-4,9-diene-3,20-dione) with the following structural formula:

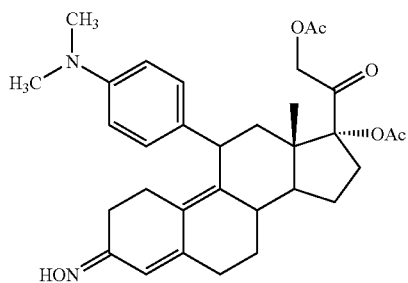

17. CDB-4226 (3-hydroxyamino-21-ethyloxy-17α-acetoxy-11β-(4 N,N-dimethylaminophenyl)-19-norpregna-4,9-diene-3,20-dione) with the following structural formula:

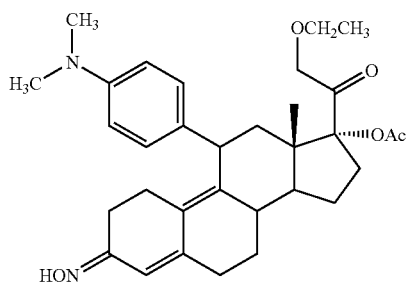

18. CDB-4262 (3-methoxyamino-21-ethyloxy-17α-acetoxy-11β-(4 N,N-dimethylaminophenyl)-19-norpregna-4,9-diene-3,20-dione) with the following structural formula:

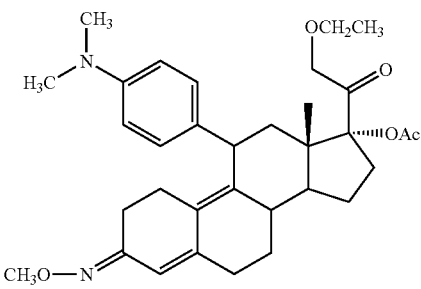

19. CDB-4223 (21-methylthio-17α-acetoxy-11β-(4 N,N-dimethylaminophenyl)-19-norpregna-4,9-diene-3,20-dione) with the following structural formula:

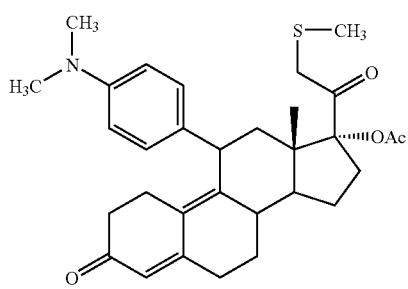

20. CDB-4119 (4-benzoin-2'-acetylthio-17α-acetoxy-11β-(4 N,N-dimethylaminophenyl)-19-norpregna-4,9-diene-3,20-dione) with the following structural formula:

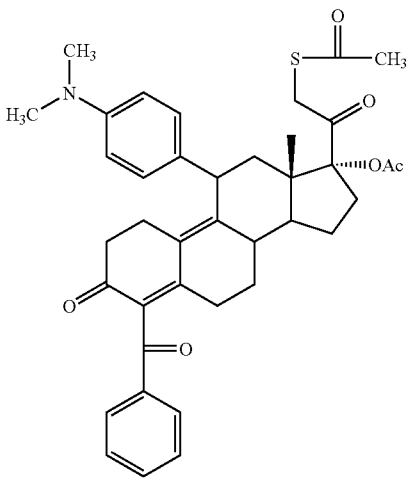

21. CDB-4239 (4-benzoin-2'-methoxy-17α-acetoxy-11β-(4 N,N-dimethylaminophenyl)-19-norpregna-4,9-diene-3,20-dione) with the following structural formula:

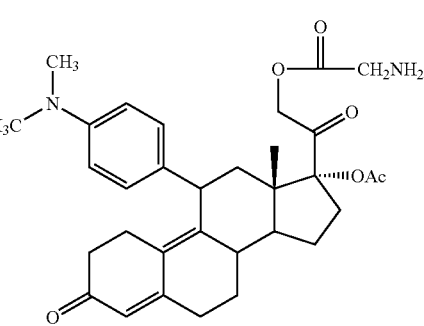

22. CDB-4306 (21-glycinate-17α-acetoxy-11β-(4 N,N-dimethylaminophenyl)-19-norpregna-4,9-diene-3,20-dione) with the following structural formula:

23. CDB-4352 (21-cyanothio-17α-acetoxy-11β-(4 N,N-dimethylaminophenyl)-19 norpregna-4,9-diene-3,20-dione) with the following structural formula:

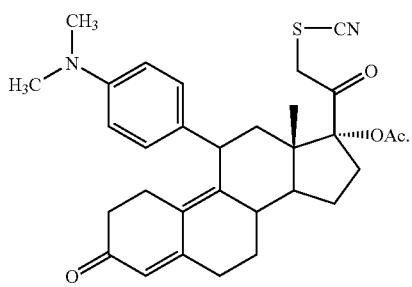 [SMILES: CC(=O)O[C@]1(C(=O)CSC#N)CCC2C3CCC4=CC(=O)CCC4=C3C(c3ccc(N(C)C)cc3)C[C@@]21C]

24. CDB-4362 (21-methoxyacetyl-17α-acetoxy-11β-(4 N,N-dimethylaminophenyl)-19-norpregna-4,9-diene-3,20-dione) with the following structural formula:

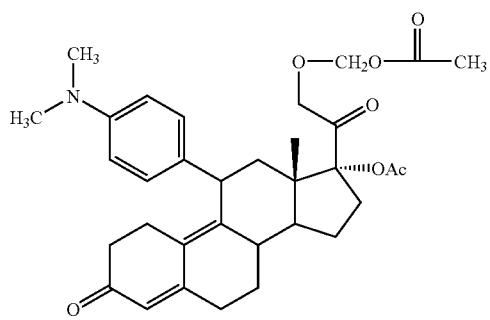

11β-monodemethylated derivatives of the 24 compounds disclosed above (i.e., those in which X is N-methylamino) are also particularly useful in practicing the instant invention. In this regard, CDB-4453 (21-methoxy-17α-acetoxy-11β-(4-N-methylaminophenyl)-19-norpregna-4,9-diene-3,20-dione), a monodemethylated derivative of CDB-4124, has been demonstrated to possess even lower anti-glucocorticoid activity than its parent. Attardi et al., 2002, Mol. Cell. Endocrin. 188:111-123, the contents of which are incorporated herein by reference.

Although compounds of the general formula above and their monodemethylated derivatives are preferred, any progesterone antagonist may be used in the practice of the present invention for its antagonist effect on the progesterone receptor. Preferably, the progesterone antagonist has one or more of the following characteristics: low antiglucocorticoid activity, minimal estrogenic and anti-estrogenic activities, and does not substantially elevate progesterone levels.

Antiprogestins which may be useful in the invention include, without limitation, asoprisnil (benzaldehyde, 4-[(11β,17β)-17-methoxy-17-(methoxymethyl)-3-oxoestra-4,9-dien-11-yl]-1-(E)-oxim; J867), its metabolite J912 (4-[17β-Hydroxy-17α-(methoxymethyl)-3-oxoestra-4,9-dien-11β-yl]benzaldehyd-(1E)-oxim), and other compounds described in DE 43 32 283 and DE 43 32 284; CDB-2914 (17α-acetoxy-11β-(4-N,N-dimethylaminophenyl)-19-norpregna-4,9-dien-3,20-dione) and other compounds described in Stratton et al., 2000, Hu. Reprod. 15:1092-1099; JNJ-1250132 and other compounds described in Allan et al., 2006, Steroids 71:949-954; 5-Aryl-1,2-dihydrochromeno[3,4-f] quinolines described in Zhi et al., 1998, J. Med. Chem. 41:291-302; 1,4-dihydro-benzo[d][1,3]oxazin-2-ones described in U.S. Pat. Nos. 6,509,334, 6,566,358 and 6,713,478 to Zhang et al.; 1,3-dihydro-indol-2-ones described in U.S. Pat. No. 6,391,907 to Fensome et al.; 2,3-dihydro-1H-indoles described in U.S. Pat. No. 6,417,214 to Ulrich et al.; benzimidazolones and analogues thereof described in U.S. Pat. No. 6,380,235 to Zhang et al.; 2,1-benzisothiazoline 2,2-dioxides described in U.S. Pat. No. 6,339,098 to Collins et al.; cyclocarbamates and cyclo-amides described in U.S. Pat. Nos. 6,306,851 and 6,441,019 to Santilli et al.; cyclic urea and cyclic amide derivatives described in U.S. Pat. No. 6,369,056 to Zhang et al.; and quinazolinone and benzoxazine derivatives described in U.S. Pat. No. 6,358,948 to Zhang et al.

Other antiprogestins that may be useful in the invention include, without limitation, (6α,11β,17β)-11-(4-dimethylaminophenyl)-6-methyl-4',5'-dihydrospiro[estra-4,9-diene-17,2'(3'H)-furan]-3-one (ORG-31710) and other compounds described in U.S. Pat. No. 4,871,724; (11β,17α)-11-(4-acetylphenyl)-17,23-epoxy-19,24-dinorchola-4,9,20-trien-3-one (ORG-33628); (7β,11β,17β)-11-(4-dimethylaminophenyl-7-methyl]-4',5'-dihydrospiro[estra-4,9-diene-17,2' (3'H)-furan]-3-one (ORG-31806) and other compounds described in U.S. Pat. No. 4,921,845; ZK-112993 and other compounds described in Michna et al., 1992, J. Steroid Biochem. Molec. Biol. 41:339-348; ORG-31376; ORG-33245; ORG-31167; ORG-31343; RU-2992; RU-1479; RU-25056; RU-49295; RU-46556; RU-26819; LG1127; LG120753; LG120830; LG1447; LG121046; CGP-19984A; RTI-3021-012; RTI-3021-022; RTI-3021-020; RWJ-25333; ZK-136796; ZK-114043; ZK-230211; ZK-136798; ZK-98229; ZK-98734; and ZK-137316.

Still other antiprogestins that may be useful in the invention include, without limitation, mifepristone (11β-[p-(Dimethylamino)phenyl]-17β-hydroxy-17-(1-propynyl)estra-4,9-dien-3-one; RU 486) and other compounds described in U.S. Pat. Nos. 4,386,085, 4,447,424, 4,519,946 and 4,634,695; the phosphorus-containing 17β-side chain mifepristone analogues described in Jiang et al., 2006, Steroids 71:949-954; onapristone (11β-[p-(dimethylamino)phenyl]-17α-hydroxy-17-(3-hydroxypropyl)-13α-estra-4,9-dien-3-one) and other compounds described in U.S. Pat. No. 4,780,461; lilopristone (((Z)-11β-[(4-dimethylamino)phenyl]-17β-hydroxy-17α-(3-hydroxy-1-propenyl)estra-4,9-dien-3-one) and other compounds described in U.S. Pat. No. 4,609,651; the 11β-substituted 19-norsteroids, such as 11β-(4-Methoxyphenyl)-17β-hydroxy-17α-ethynyl-4,9-estradien-3-one described in Belagner et al., 1981, Steroids 37:361-382; the 11β-aryl-4-estrenes such as (Z)-11β-[(4-Dimethylamino)phenyl)]-17β-hydroxy-17α-(3-hydroxy-1-propenyl)estr-4-en-3-one described in U.S. Pat. No. 5,728,689; the 11β-aryl-estrene derivatives described in U.S. Pat. Nos. 5,843,933 and 5,843,931; the 11-benzaldoxime-estra-diene derivatives such as 4-[17β-Methoxy-17α-(methoxymethyl)-3-oxoestra-4,9-dien-11β-yl]benzaldehyde-1-(E)-oxime described in U.S. Pat. No. 5,693,628; the 11-benzaldoxime-17β-methoxy-17α-methoxymethyl-estradiene derivatives such as 4-[17β-Methoxy-17α-(methoxymethyl)-3-oxoestra-4,9-dien-11β-yl]benzaldehyde-1-(E)-[O-(ethylamino)carbonyl]oxime described in U.S. Pat. No. 5,576,310; the S-substituted 11β-benzadoxime-estra-4,9-diene-carbonic acid thiolesters such as 4-[17β-Methoxy-17α-(methoxymethyl)-3-oxoestra-4,9-dien-11β-yl]benzaldehyde-1-(E)[O-(ethylthio)carbonyl] oxime, described in WO 99/45023; the steroid esters such as (Z)-6'-(4-cyanophenyl)-9,11α-dihydro-17β-hydroxy-17α-[4-(1-oxo-3-methylbutoxy)-1-butenyl]-4'H-naphtho[3',2',1'; 10,9,11]estr-4-en-3-one described in DE 19652408, DE 4434488, DE 4216003, DE 4216004 and WO 98/24803; the fluorinated 17α-alkyl chain steroids such as 11β-(4-acetylphenyl)-17β-hydroxy-17α-(1,1,2,2,2-pentafluoroethyl)estra-4,9-dien-3-one described in WO 98/34947; the 17-spirofuran-3'-ylidene steroids such as 11beta-(4-Acetylphenyl)-19,24-dinor-17,23-epoxy-17alpha-chola-4,9,20-trien-3-one described in U.S. Pat. No. 5,292,878; (Z)-11beta,19-[4-(3-Pyridinyl)-o-phenylene]-17beta-hydroxy-17α-[3-hydroxy-1-propenyl]-4-androsten-3-one and other compounds described in U.S. Pat. No. 5,439,913; the 13-alkyl-11-beta-phenyl gonanes such as 11beta-[4-(1-methylethenyl)phenyl]-17α-hydroxy-17beta-(3-hydroxypropyl)-13α-estra-4,9-dien-3-one described in U.S. Pat. No. 5,446,036; the 11-arylsteroids such as 4',5'-Dihydro-11beta-[4-(dimethylamino)phenyl]-6beta-methylspiro[estra-4,9-dien-17beta,2'(3'H)-furan]-3-one described in U.S. Pat. No. 4,921,845; the 11-beta-aryl-estradienes described in U.S. Pat. Nos. 4,829,060, 4,814,327 and 5,089,488; the 11-beta-aryl-4,9 gonadiens and 11-beta-aryl-13-alkyl-4,9-gonadiens described in U.S. Pat. Nos. 5,739,125, 5,407,928 and 5,273,971; the 11-beta-aryl-6-alkyl (or alkenyl or alkinyl) steroids described in EP 289073; the 10-beta,11-beta-bridged steroids described in U.S. Pat. No. 5,093,507; the 11-beta-aryl-14-beta-steroids described in U.S. Pat. No. 5,244,886; the 19,11-beta-bridged steroids described in U.S. Pat. Nos. 5,095,129, 5,446,178, 5,478,956 and 5,232,915; the 1-arylsulphonyl, arylcarbonyl and 1-arylphosphonyl-3-phenyl-1,4,5,6-tetrahydropyridazines described in U.S. Pat. No. 5,684,151; the 1-arylsulphonyl, arylcarbonyl and arylthiocarbonyl pyridazino derivatives described in U.S. Pat. No. 5,753,655; the 1,2-dihydro-[1,2-g]quinoline derivatives and 1,2-dihydro-chromeno-[3,4-f]quinoline derivatives described in U.S. Pat. Nos. 5,688,808, 5,693,646, 5,693,647, 5,696,127, 5,696,130 and 5,696,133; the oxa-steroids 6 derived from (8S,13S,14R)-7-oxa-estra-4,9-diene-3,17-dione 1 described in Kang et al., 2007, Bioorg. Med. Chem. Lett. 15:907-910; and the 7-oxa-steroids 4 described in Kang et al., 2007, Bioorg. Med. Chem. Lett. 17:2531-2534.

In the preferred embodiment, the progesterone antagonist is the antiprogestin/SPRM CDB-4124 (21-methoxy-17α-acetoxy-11β-(4 N,N-dimethylaminophenyl)-19-norpregna-4,9-diene-3,20-dione). Example 10 demonstrates that administration of CDB-4124 at a high dosage (50 mg/day) suppresses endometrial proliferation in adult females, but does not suppress endometrial proliferation at lower dosages (25 mg/day and 12.5 mg/day).

Progesterone antagonist compositions of the instant invention may be given to patients undergoing any hormone therapy associated with an increased risk or incidence of endometrial hyperplasia or endometrial cancer. These treatments may include, but are not limited to, the administration of estrogens or the administration of SERMs. Progesterone antagonist compositions of the instant invention can be also given to patients undergoing antiestrogenic treatments because the patients may benefit from antiproliferative effects that progesterone antagonist compounds exert in endometrial tissue of the uterus.

SERMs are currently administered to treat various disorders including breast cancer, osteoporosis, colon cancer, neurodegenerative diseases such as Parkinson and Alzheimer, cardiovascular disease, vaginal atrophy and obesity. However, SERM therapy is associated with endometrial hyperplasia and endometrial cancer. For example, Tamoxifen treatment of breast cancer results in about a 20% incidence of hyperplasia with atypia in women with intact uteri. Patients with endometrial specimens displaying atypia have a 25% likelihood of progressing to carcinoma. Compounds of the present invention are administered at doses sufficient to oppose the hyperplasia that accompanies treatment with SERMs. The compounds of the present invention may be administered in combination with SERMs for the treatment of any of the aforementioned disorders.

Estrogens are currently administered as part of hormone replacement therapy (HRT) to postmenopausal women who no longer produce estrogens. However, estrogen-only therapy is considered unsafe for menopausal women with intact uteri because of the accompanying endometrial hyperplasia. Co-administration of progestin is frequently proscribed to oppose the hyperproliferative effects of estrogen; however, the addition of progestin has been linked to breast cancer in the WHI studies and can result in break-through bleeding. The compounds of the present invention may be administered in combination with estrogens as part of a hormone replacement regimen.

The compounds disclosed in the instant invention may act as progesterone antagonists in the uterus. The compounds of the instant invention may be suitable for the prolonged usage required in menopausal patients undergoing hormone replacement therapy, as for other indications. Where such usage is considered, the compounds preferably have only low glucocorticoid receptor binding activity and therefore, the compounds do not substantially interfere with functions of glucocorticoid receptor. Thus, the application of the compounds may have reduced side effects, such as mood swings, fatigue and weight loss, typically found when antiprogestins with a high affinity for glucocorticoid receptor are used.

In another embodiment the instant invention teaches methods that can be used for identifying compounds that possess selective progesterone receptor binding activity. These methods include receptor binding and in vivo bioassays such as anti-McGinty, anti-Clauberg, glucocorticoid, estrogenic, androgenic, anti-glucocorticoid (AG), anti-estrogen, and anti-androgen activities as well as post-coital and anti-ovulatory activities where in the leading compounds of the instant invention are used as a reference.

In another embodiment, the instant invention teaches that the potential SPRMs can be also analyzed for their effect on transcriptional activity in human cells. When SPRMs disclosed in the instant invention are used as a reference, this analysis can furnish information about (1) SPRM's interaction with receptor, (2) interaction of the activated receptor with other transcription factors, (3) activation of a transcriptional complex at a progesterone response element (PRE); and ultimately its effect on gene expression. In these experiments, plasmid expressing the hPR-B can be cotransfected with any reporter known to a person skilled in the relevant art under the PRE-dependent promoter into HeLa, HepG2 or T47D cells. The reporters may include, but are not limited to, luciferase, beta-galactosidase, green fluorescent protein, red fluorescent protein or yellow fluorescent protein. After transfection, the cells are treated with either a test compound or one of the disclosed in this application SPRMs that serves as a positive control. Following treatment, cells are assayed for reporter expression.

In another embodiment, the instant invention teaches that prospective SPRMs can be tested for their ability to oppose dexamethasone-induced cell death in human lymphocytic cell line CEM-7 and compared to effects of SPRMs disclosed in the instant specification. In these experiments, dexamethasone can be added at a concentration that results in cell death. The cells are then treated with either RU486, one of SPRMs of the instant invention or a test compound at concentrations between $10^{-6}$ and $10^{-8}$ M.

Progesterone antagonist compounds that may be used in accordance with the present invention can be synthesized using synthetic chemistry techniques known in the art such as those disclosed in U.S. Pat. No. 6,861,415. It is to be understood that certain functional groups may interfere with other reactants or reagents under the reaction conditions and therefore may need temporary protection. The use of $2^{nd}$ protecting groups is described in 'Protective Groups in Organic Synthesis', edition, T. W. Greene & P. G. M. Wutz, Wiley-Interscience (1991).

In one embodiment, compositions of the invention comprise one or more progesterone antagonists or pharmaceutically acceptable salts thereof. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbenzenesulfonic acid, toluenesulfonic acid, galactaric acid, galacturonic acid or naphthalenesulfonic acid. All crystalline form polymorphs may be used in accordance with the invention.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like For the aforementioned purposes, the compounds of the instant invention can be administered to a patient via any conventional route where the progesterone antagonist is active. For instance, a progesterone antagonist of the instant invention can be administered orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, intraarticular, intracisternal and intraventricular. The administration form can be a tablet, capsule, pill, nasal mist, aerosol, pellet, implant (or other depot) and the like.

A therapeutically effective amount of the composition required for use in therapy may vary depending on the particular compound employed, the mode of administration, the severity of the condition being treated, the length of time that activity is desired, among other factors, and is ultimately determined by the attendant physician. In all cases, an effective dosage of a particular compound is one that is sufficient to suppress endometrial proliferation. However, in general, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a composition of the invention may be administered to a subject to provide the subject with a progesterone antagonist in an amount of about 1 µg/kg to about 1 mg/kg body weight, for example about 1 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg or about 1 mg/kg body weight.

The compositions of the instant invention may contain from about 25 to about 90% of the active ingredient in combination with the carrier, more usually between about 5% and 60% by weight.

Solid carriers may include starch, lactose, dicalcium phosphate, microcrystalline cellulose, sucrose and kaolin, while liquid carriers may include sterile water, polyethylene glycols, non-ionic surfactants and edible oils such as corn, peanut and sesame oils, as are appropriate to the nature of the active ingredient and the particular form of administration desired. Flavoring agents, coloring agents, preserving agents, and antioxidants, for example, vitamin E and ascorbic acid, may be included in preparations as well. Under ordinary conditions of storage and use, the preparations may contain a preservative to prevent the growth of microorganisms.

The compositions of the instant invention can be formulated into tablets in a tablet press by using techniques well-known to an artisan skilled in the relevant field. Optionally, the active ingredients according to the invention can also be pressed separately into two-layer tablets. According to the instant invention, tablets may include antiestrogens, estrogens or SERMs as one of the active ingredients. Compositions of the instant invention can also be formulated as an oily solution.

Patients undergoing treatments with the compositions of the instant invention should be monitored routinely for their serum estrogen and glucocorticoid levels.

The following non-limiting examples are provided to aid in understanding the teachings of the instant invention.

All patents, patent applications and publications referenced herein are hereby incorporated by reference herein to the fullest extent allowed under the law.

Example 1

Formulations of the Instant Invention can be Prepared as Tablets

To obtain tablets for practicing the instant invention, the following ingredients can be pressed together in a tablet press:

| | |
|---|---|
| 50.0 mg | of CDB-4124 |
| 140.5 mg | of lactose |
| 69.5 mg | of corn starch |
| 2.5 mg | of poly-N-vinylpyrrolidone |
| 2.0 mg | of aerosil |
| 0.5 mg | of magnesium stearate |

To obtain two-layer tablets for practicing the instant invention, the following ingredients can be pressed together in a tablet press:

| | |
|---|---|
| 20.0 mg | of Tamoxifen |
| 50.0 mg | of CDB-4124 |
| 105.0 mg | of lactose |
| 40.0 mg | of corn starch |
| 2.5 mg | of poly-N-vinylpyrrolidone 25 |
| 2.0 mg | of aerosil |
| 0.5 mg | of magnesium stearate |

To obtain tablets containing antiestrogens for practicing the instant invention, for example, the following ingredients can be pressed together in a tablet press:

| | |
|---|---|
| 10.0 mg | of Raloxifene |
| 50.0 mg | of CDB-4124 |
| 125.0 mg | of lactose |
| 50.0 mg | of corn starch |
| 2.5 mg | of poly-N-vinylpyrrolidone 25 |
| 2.0 mg | of aerosil |
| 0.5 mg | of magnesium stearate |

To obtain oily preparations for practicing the instant invention, for example the following ingredients can be mixed together and loaded into ampoules:

| | |
|---|---|
| 100.0 mg | of CDB-4124 |
| 343.4 mg | of castor oil |
| 608.6 mg | of benzyl benzoate |

Example 2

Compounds of the Instant Invention May have Only Weak Antiglucocorticoid Receptor Binding Activity Certain antiprogestins were tested in receptor-binding assays for their ability to bind rabbit progesterone receptor (rbPR) and glucocorticoid receptor (rbGR). Briefly, cytosol containing PR or GR were prepared in TEGMD buffer (10 mM Tris, pH 7.2, 1.5 mM EDTA, 0.2 mM sodium molybdate, 10% glycerol, 1 mM DTT) from uterus or thymus, respectively, of estradiol-primed immature rabbits. For PR binding, the cytosol was incubated with 6 nM 1,2-[$^3$H]progesterone (50.0 Ci/mmole) and competitors were added at concentrations from 2 to 100 nM. For binding to GR, the cytosol was incubated with 6 nM 6,7-[$^3$H]-dexamethasone (40 Ci/mmol) and test compounds were added at concentrations from 20 to 100 nM. After overnight incubation at 4 C, bound and unbound [$^3$H] steroids were separated by addition of dextran-coated charcoal and centrifugation at 2100×g for 15 min at 4 C. Supernatants containing the [$^3$H]-steroid receptor complexes were decanted into vials containing 4 ml OPTIFLUOR scintillation fluid (Packard Instrument Co.), vortexed, equilibrated in a liquid scintillation counter for 30 minutes and then counted for 2 minutes. The $EC_{50}$ (Effective Concentration) for each standard curve and each of the compound curves was determined by entering the counting data into a four parameter sigmoidal computer program (RIASMART Immunoassay Data Reduction Program, Packard Instrument Co., Meriden, Conn.). Relative binding affinity (RBA) for each compound was calculated using the following equation: $EC_{50}$ of standard/$EC_{50}$ of test compound×100. The standards for the PR and GR assays were unlabeled progesterone and dexamethasone, respectively. The results of these experiments are summarized in Table 1, as a ratio of the relative binding affinities of each compound for the rbPR and rbGR receptors (rbPR/rbGR). This differential reflects the relative activity of a compound in a cell or tissue that possesses the two receptors and the requisite transcriptional cofactors.

Also given in Table 1 are the relative biological activities of the same compounds in the rabbit uterus by the anti-McGinty and anti-Clauberg assays. Compound CDB-2914 (listed at the end of the Table) was used as the control or reference compound (rabbit Biological Activity=1.00) for these experiments because results of experiments using CDB-2914 have been published before (Hild-Petito et al., 1996; Passaro et al., 1997; Reel et al., 1998; Larner et al., 2000). For the anti-McGinty test, immature female rabbits received a subcutaneous injection of 5 µg estradiol in 10% ethanol/sesame oil daily for 6 consecutive days. On day 7, animals underwent sterile abdominal surgery to ligate a 3-4 cm segment of both uterine horns. The test compound in appropriate solvent was injected intraluminally into the ligated segment of one uterine horn and vehicle alone into the other. A stimulating dose of progesterone (267 µg/day) was administered subcutaneously to each rabbit daily for the next three days to induce endometrial proliferation. All animals were sacrificed at day 10 for removal of the uterus where a segment central to the ligatures was removed and fixed in 10% neutral buffered formalin and submitted for histological processing. Five micron sections stained with hematoxylin and eosin were evaluated microscopically for the degree of endometrial glandular proliferation. The percent inhibition of endometrial proliferation for each rabbit was calculated and the mean of the group of five animals recorded. For the Anti-Clauberg test, immature female rabbits received a subcutaneous injection of 5 µg estradiol in 10% ethanol/sesame oil daily for 6 consecutive days. On day 7, animals received progesterone by subcutaneous injection (160 µg/day) and the experimental compound in appropriate vehicle orally or subcutaneously for five consecutive days. One group of rabbits received progesterone only. Twenty-four hours after the last dose, all animals were sacrificed for removal of the uterus which was cleaned of all fat and connective tissue, weighed to the nearest 0.2 mg and placed in 10% neutral buffered formalin for subsequent histological processing. Five micron sections stained with hematoxylin and eosin were evaluated microscopically for the degree of endometrial glandular proliferation. The percent inhibition of endometrial proliferation at each dose level of the test compound was derived by comparison with progesterone-stimulated animals alone. The data presented in Table 1 (rabbit Biol. Act.) reflects the average of the results obtained for each compound by the anti-McGinty and anti-Clauberg assays relative to CDB-2914.

The tested antiprogestins were ranked on the basis of the selectivity of each compound for the rabbit PR over the rabbit GR, as listed in Table 1. The antiprogestins were also ranked on the basis of the biological activity in the rabbit uterus. Data presented in Table 1 show that the affinity of leading compounds for progesterone receptor was at least 1.5 times greater than their affinity for glucocorticoid receptor.

The results of these studies also show that the two leading compounds CDB-4124 and CDB-4059 have strong antiprogestin activity in the rabbit uterus in comparison to RU 486 and CDB-2914. Both compounds lack estrogenic, androgenic, anti-estrogenic, and anti-androgenic activities. Both compounds possess minimal anti-glucocorticoid receptor activity, a feature that distinguishes them from RU 486 and CDB-2914 which are moderately active in glucocorticoid receptor binding. In these assays, CDB-4124 performed slightly better than CDB-4059

TABLE 1

RECEPTOR BINDING AND BIOLOGICAL ACTIVITIES OF SPRMS

| SPRM | rbPR/rbGR | rabbit Biol. Act. | SPRM | rbPR/rbGR | rabbit Biol. Act. |
|---|---|---|---|---|---|
| 4239 | 14.80 | 0.60 | 4416 | 1.33 | 0.77 |
| 4241 | 9.10 | 0.34 | 4417 | 1.31 | 0.70 |
| 4361 | 7.20 | 3.03 | 4111 | 1.30 | 0.36 |
| 4306 | 5.90 | 0.95 | 4125 | 1.19 | 1.55 |
| 4363 | 5.75 | 2.53 | 4223 | 1.17 | not given |
| 3875 | 5.11 | 1.40 | 4398 | 1.16 | 0.99 |
| 4362 | 4.74 | 1.25 | 4058 | 1.08 | 0.90 |
| 4352 | 4.21 | 0.57 | 4418 | 1.03 | 0.25 |
| 4176 | 3.83 | 0.20 | 4177 | 1.03 | 0.00 |
| 4243 | 2.90 | 0.00 | 4030 | 0.96 | 0.30 |
| 4119 | 2.60 | 0.10 | 4374 | 0.95 | 2.25 |
| 4324 | 2.16 | 1.10 | 4399 | 0.93 | 0.35 |
| 4247 | 2.06 | 1.70 | 4152 | 0.82 | 1.40 |
| 4205 | 1.99 | 1.00 | 4110 | 0.70 | 0.10 |
| 4059 | 1.89 | 2.90 | 4031 | 0.69 | 0.70 |
| 4400 | 1.76 | 2.29 | 4101 | 0.61 | 0.65 |
| 3247 | 1.74 | 0.10 | 4248 | 0.42 | 0.00 |
| 4167 | 1.69 | 1.50 | 4227 | 0.38 | 0.00 |
| 4124 | 1.58 | 3.60 | 4393 | 0.35 | 0.00 |
| 4226 | 1.51 | 0.54 | 4396 | 0.18 | not given |
| 4206 | 1.44 | 0.68 | 2914 | 1.07 | 1.00 |

Example 3

Measuring Cortisol

Several different experimental systems support a conclusion that RU 486 increases cortisol because RU 486 has strong anti-glucocorticoid properties in humans and primates.

However, as shown in FIG. 1, rats treated with RU 486 at 10 mg/kg showed no significant difference in the levels of cortisol. In contrast, rats treated with either CDB-4124 or CDB-4059 at the same dose levels had significantly higher levels of serum cortisol than rats from a control group.

Figure 2:
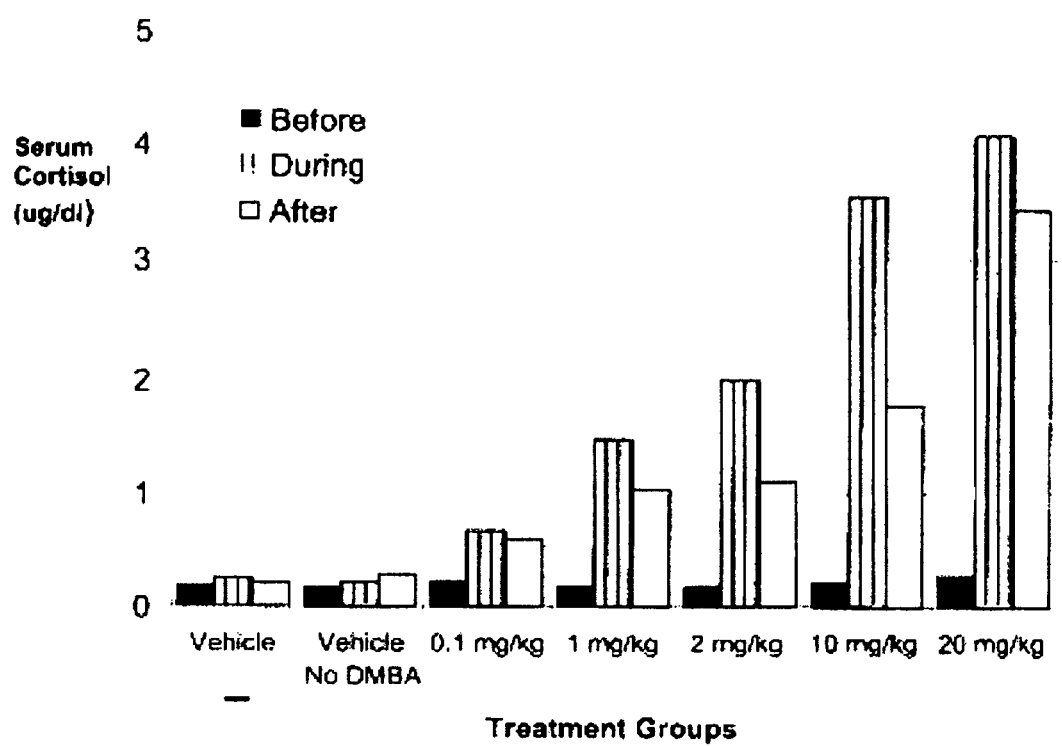
FIG. 2 is a graph depicting the dose-dependent effect of CDB-4124 on serum cortisol in rats.

These higher levels were in the range of 3-4 ug/dl (30-40 ng/ml). The effects were dose-dependent in that increasing doses of CDB-4124 led to increased cortisol (FIG. 2).

This difference in effects of RU 486 versus CDB-4124 or CDB-4059 on cortisol levels can be explained by assuming that after 21 days of chronic dosing, a rat liver was able to metabolize RU 486 better than either of the two CDB compounds.

Example 4

Measuring Corticosterone

Corticosterone is the most abundant glucocorticoid in rats. The effects of the SPRMs on cortisol shown in FIGS. 1 and 2 may be secondary to strong effects on corticosterone. To better explore this phenomenon, the levels of corticosterone were measured in groups, which showed the strongest changes in cortisol levels, such as groups treated with CDB-4124 at 20 mg/kg or 10 mg/kg. For comparison, the following groups were also assayed: a group that received 20 mg/kg CDB-4124 plus 10 mg/kg progesterone, a group that received 10 mg/kg CDB-4124 plus 10 mg/kg progesterone, a group that received 10 mg/kg RU 486, a group that received 10 mg/kg of progesterone alone, a control group. The levels of corticosterone were 10-40 times higher than the levels of cortisol. However, almost no difference between groups with respect to mean corticosterone levels was observed. There were no differences among the groups before treatment (p=0.43, Kruskal-Wallis test), after 21 days of treatment (p=0.57, Kruskal-Wallis test), or after 28 days of treatment and at sacrifice (p=0.061, Kruskal-Wallis test.

To measure effects of exogenous progesterone on serum corticosterone, the levels of corticosterone were compared in 3 paired groups that differed in whether they received exogenous progesterone (e.g., comparisons of control versus progesterone or CDB-4124 at 20 mg/kg versus CDB-4124 at 20 mg/kg plus progesterone, or CDB-4124 at 10 mg/kg versus CDB-4124 at 10 mg/kg plus progesterone). There was a statistically significant difference detected: the levels of corticosterone were lowered in animals treated with progesterone after 21 days of treatment (p=0.029, Mann-Whitney Wilcoxon test, two-tailed). This effect was not verified in sera taken at sacrifice. No differences in serum corticosterone were found between the progesterone and the CDB-4124 groups, the progesterone and the RU-486 groups, or the RU-486 group and the CDB-4124 groups.

The relationship between serum cortisol and serum corticosterone in each group was also examined. There was a strong positive linear correlation between the two for CDB-4124 at 20 mg/kg ($r^2=0.78$), for CDB-4124 at 10 mg/kg ($r^2=0.82$), and for RU 486 ($r^2=0.85$). Adding progesterone to the first two CDB-4124 groups made the relationship far less strong ($r^2=0.34$ for Group 10 and $r^2=0.37$ for Group 11, respectively). Progesterone itself showed no such positive relationship ($r^2=-1.0$). The control group demonstrated no relationship between the two glucocorticoids ($r^2=0.064$). Thus, increased levels of cortisol in groups receiving CDB-4124 are correlated to levels of corticosterone, due perhaps to conversion from corticosterone that is somehow enhanced. This is consistent with an effect of CDB-4124 seen above: an effect on metabolic enzymes responsible for levels of progesterone and cortisol.

Although no strong effect of CDB-4124 on the primary glucocorticoid of the rat was found, nevertheless, for safety reasons, patients given CDB-4124 or CDB-4059 in Phase I clinical trials should be monitored for possible anti-glucocorticoid effects including a possible increase in serum cortisol, corticosterone, or ACTH.

Example 5

Testing Anti-Proliferative Effects of SPRMs in Uterine Cells

Any uterine cell lines can be used. Proliferation is measured in 96-well microtiter plates. $5 \times 10^3$ cells are added to each well. Culture medium and drug solutions are added to wells with a Perkin Elmer Cetus PRO/PETTE. The culture medium is IMEM supplemented with 5% fetal bovine serum. Eight drug concentrations are tested, in duplicate, from 0.078 uM to 10 uM. Samples include tamoxifen alone and each of the compounds disclosed in the instant specification in combination with tamoxifen.

After a four-day incubation, the medium is replaced with fresh medium containing drug, and after a total of seven days, the cell monolayers are fixed with trichloracetic acid and stained with sulforhodamine dye. Absorbances (492 nm) of the extracted dye solutions are measured with a Titertek Multiscan plate reader. Dose response curves (percent of control absorbances vs. drug concentrations) are constructed in order to estimate $IC_{50}$ values defined as the drug concentrations (micromolar) which inhibited 50% proliferation. $IC_{50}$ values are correlative with a potency of a tested drug in inhibiting cell proliferation and therefore provide information required to identify compounds suitable for preventing hyperproliferation of the uterine cells.

Example 6

CDB-4124 Lowers Luteal Phase Progesterone in Cynomolgus Monkeys

Cynomolgus monkeys (*Macaca fascicularis*) (n=14) were treated orally for 36 weeks with CDB-4124 or RU-486 at 1.0 mg/kg/day or with placebo (control). Another group (n=14) received LUPRON IM once per month. Urinary progesterone levels were measured for each animal for one month during the middle of the study (weeks 14-17) and for the last month of the study (weeks 33-36). The results are presented below:

|  | Decrease in luteal phase progesterone | No decrease in luteal phase progesterone |
|---|---|---|
| Controls | 1 | 13 |
| LUPRON | 13 | 1 |
| RU 486 | 9 | 5 |
| CDB-4124 | 8 | 6 |

Example 7

CDB-4124 does not Lower Follicular Phase Estrogen in Cynomolgus Monkeys

Urinary estrogen levels were measured for each animal of Example 6 for one month during the middle of the study (weeks 14-17) and for the last month of the study (weeks 33-36). The follicular phase results are based on 35 baseline ovulating cycles. The results are presented below:

|  |  | Mean | Sd | Lower? |
|---|---|---|---|---|
| Follicular Phase |  | 68.3 | 19.6 |  |
| Controls | Week 18 | 81.5 | 27.4 | No |
|  | Week 36 | 86.3 | 23.8 | No |
| LUPRON | Week 18 | 49.9 | 19.3 | Yes |
|  | Week 36 | 41.7 | 13.4 | Yes |
| RU 486 | Week 18 | 67.4 | 27.1 | No |
|  | Week 36 | 64.8 | 30.0 | No |
| CDB-4124 | Week 18 | 63.8 | 24.6 | No |
|  | Week 36 | 67.3 | 22.9 | No |

Example 8

CDS-4124 and LUPRON but not RU 486 Suppress Proliferation in Cynomolgus Monkey Endometrial Epithelia At week 36, three animals from each group of Example 6 were injected within 24 hours of sacrifice with the thymidine analog bromodeoxyuridine (BrdU), a marker of proliferating cells and their progeny, to assess tissue proliferation. Full thickness uterine sections were stained and examined microscopically for evidence of proliferation in terms of the % cells positive for incorporation of BrdU:

| TXT | Uterus epithelium Brdu-% | Uterus stroma Brdu-% | Breast Brdu-% |
|---|---|---|---|
| Control | 10.0 ± 2.5 | 2.6 ± 0.6 | 2.4 ± 1.1 |
| LUPRON | 3.1 ± 0.8 | 2.2 ± 1.0 | 0.3 ± 0.1 |
| RU 486 | 12.6 ± 1.8 | 3.1 ± 1.0 | 0.9 ± 0.3 |
| CDB-4124 | 2.1 ± 2.2 | 1.1 ± 0.25 | 1.9 ± 0.7 |

Example 9

CDB-4124 and RU 486 but not LUPRON Enhance Apoptosis in Cynomolgus Monkey Endometrial Epithelium Apoptosis was assessed in tissue from the same animals on slides by the terminal deoxynucleotidyl transferase mediated dUTP-biotin nick end labeling (TUNEL) technique. The percent apoptotic cells is presented below:

| TXT | Uterus epithelium Apo % | Uterus stroma Apo % | Breast Apo % |
|---|---|---|---|
| Control | 0.2 ± 0.1 | 0.7 ± 0.2 | 0.5 ± 0.3 |
| LUPRON | 0.2 ± 0.1 | 0.2 ± 0.1 | 1.4 ± 0.7 |
| RU 486 | 0.5 ± 0.1 | 0.5 ± 0.1 | 1.2 ± 0.6 |
| CDB-4124 | 0.5 ± 0.2 | 0.5 ± 0.1 | 2.6 ± 0.9 |

Example 10

CDB-4124 Suppresses Proliferation in Human Endometrial Epithelia in a Dose-Dependent Manner Thirty-nine pre-menopausal adult women diagnosed with endometriosis were the subject of a six month study of Proellex™ (CDB-4124) in the treatment of endometriosis. The study included three dose levels of CDB-4124 as well as a positive control arm. The positive control was LUCRIN, a GnRH agonist, commonly used for the treatment of endometriosis (also known as LUPRON. CDB-4124 was administered in a double blinded fashion as a daily oral capsule at dosages of 12.5 mg/day (n=2), 25 mg/day (n=3) and 50 mg/day (n=3). Another group (n=4) were injected with a slow release formulation of LUCRIN once per month as a positive control.

All doses of CDB-4124, as well as the LUCRIN dose, on average reduced distress related to pain over the course of the six month exposure to the drug, with the 50 mg CDB-4124 dose reducing both the duration and intensity of pain more effectively than the 12.5 mg or 25 mg doses and is significantly better (p=0.0012) than LUCRIN in reducing the number of days of pain over the course of the study. Pain reduction also occurred more rapidly than with the active control, LUCRIN. The response of pain to treatment in this study was analyzed in two ways. Patients in the study maintained daily pain diaries to record the severity and frequency of pain. In addition, at each office visit, patients filled out endometriosis symptom surveys that included a questionnaire that evaluated intensity of pain on a bad day on a scale of 0-10 with 10 being the greatest intensity. Daily pain diaries indicated that on average, women on LUCRIN experienced 19.4 days of pain over the first three months. Women on 50 mg of CDB-4124 exhibited less than 1 day of pain over the same period. Women on 25 mg and 12.5 mg of CDB-4124 exhibited more days of pain than that recorded by women receiving the highest dose of CDB-4124 or LUCRIN. There appeared to be a dose dependent effect on pain reduction. Over the 180 day treatment period, pain diaries indicated that women on the 50 mg CDB-4124 dose had 170 or 96% pain free days (standard deviation=8.86 days). This decrease in duration of pain was statistically better (p=0.0012) than the 117.8 (74%; standard deviation 51.4 days) pain free days achieved with LUCRIN. The 50 mg dose of CDB-4124 was also statistically superior to both the 25 mg and the 12.5 mg doses with regard to pain free days. Patients on CDB-4124 12.5 mg and 25 mg doses had 115.9 (66%; standard deviation 69.2 days) and 133.6 (75%; standard deviation 27.4 days) pain free days, respectively. These results clearly support a dose response for CDB-4124. The 25 mg and 12.5 mg doses of CDB-4124 were not statistically different from LUCRIN. At the end of the first month of therapy there was a statistically significant reduction in days of pain in the 50 mg Proellex group (p=0.031) compared with baseline, but not in the three other treatment groups. The intensity of pain was asked by the question: "On a scale of 1-10, with 0 being no pain and 10 being extreme pain, how intense was your pain on a bad day?" The mean scores for intensity of pain at baseline were 6.3 for the CDB-4124 groups and 6.1 for the LUCRIN group. Statistically significant relief from pain was evident by the first month in the 25 mg and 50 mg Proellex groups. At month three all four active treatment groups had statistically significant reduction in pain compared with baseline, with the following scores: 3.7 (p=0.03) for 12.5 mg CDB-4124, 3.2 (p=0.03) for 25 mg CDB-4124, 1.6 (p=0.015) for 50 mg CDB-4124 and 1.5 (p=0.016) for LUCRIN. These dose related reductions continued until month six when the values for pain intensity were 2.0 (p=0.008), 2.8 (p=0.023), 0.6 (p=0.004) and 0.7 (p=0.016), respectively. Two months after stopping treatment pain returned and was of similar intensity in all four treatment groups.

Women receiving LUCRIN in the study, on average, experienced a reduction of estrogen to post-menopausal levels (<20 pg/ml) by month three and this was maintained through month six of treatment. This outcome was associated with a statistically significant increase (p=0.023) in biomarkers of bone resorption compared with the baseline values at month three, and therefore an increased risk of bone loss. At month six as well as at the one-month follow up visit, this increase in markers of bone resorption was still present in women treated with LUCRIN. All doses of CDB-4124 maintained estrogen concentrations significantly above those seen with LUCRIN and remained in the low normal range (mean>40 pg/ml). Importantly, there were no significant changes in biomarkers of bone resorption in any of the dose arms of CDB-4124 at three and six months of treatment. Women with post-menopausal levels of estrogen have been shown to be at greater risk for bone loss and other medical conditions. LUCRIN, therefore, is not indicated for treatment lasting longer than six months.

Side effects of CDB-4124 were generally mild with no individual organ system being involved systematically. Although this was a small study and no definitive conclusions can be made from the safety data, there was no single signal of safety observed.

Women in the study were closely monitored for changes in the structure of the endometrium. Data from these examinations suggest an inverse dose dependent effect of CDB-4124 on endometrial thickness at the three month period. Comparisons were made to both baseline and visit one ultrasound measurements of endometrial thickness. After three months on treatment none of the women receiving the 50 mg dose of CDB-4124 (n=3) exhibited thickened endometrium and actually exhibited a trend toward reduction in endometrial thickness compared to baseline. One woman receiving the 25 mg dose of CDB-4124 (n=4) and two women receiving the 12.5 mg dose of CDB-4124 (n=4) exhibited a thickened endometrium. The five women who received LUCRIN did not have a thickening of the endometrium due to a low estrogenic state. The results are presented below:

|  | Endometrium (mm) | | |
| --- | --- | --- | --- |
|  | screening | 1$^{st}$ dose | 3 months |
| LUPRON | 7.9 | 7.5 | 2.75 |
| CDB-4124 (12.5 mg) | 7.5 | 8.0 | 20.33 |
| CDB-4124 (25 mg) | 8.4 | 11.7 | 19.6 |
| CDB-4124 (50 mg) | 8.0 | 10.8 | 7.7 |

In two cases where non-menstrual spotting and bleeding was observed in patients with excessive endometrial thickening in the 12.5 mg and 25 mg CDB-4124 groups, a dilation and curettage (D&C) procedure was performed to stop the bleeding. A similar event was not seen at the 50 mg dose during the treatment phase. Greater than normal bleeding occurred in two patients in the 50 mg CDB-4124 group after treatment was stopped and a D&C was performed in one and the other successfully managed conservatively.

I claim:

1. A method for treating endometriosis according to an intermittent administration regimen comprising administering to a human female in need of such treatment 2 to 80 mg of a selective progesterone receptor modulator (SPRM) selected from CDB-4124 (21-methoxy-17α-acetoxy-11β-(4-N,N-dimethylaminophenyl)-19-norpregna-4,9-diene-3,20-dione) and 17α-acetoxy-11β-(4-N,N-dimethylaminophenyl)-19-norpregna-4,9-dien-3,20-dione for an administration period during which the SPRM is administered daily consecutively over a period of two to four months, then discontinuing said administration for a period of time sufficient for the female to undergo menstruation, said period of time being at least 32 days and equal to or less than the number of days during which the SPRM was previously administered, then administering 2 to 80 mg of the SPRM daily consecutively over a period of two to four months, then discontinuing said administration for a period of time sufficient for the female to undergo menstruation, said period of time being at least 32 days and equal to or less than the number of days during which the SPRM was previously administered, and repeating this pattern of administration and discontinuation of administration for a sufficient duration to treat the endometriosis, wherein the female is administered a progestin in an amount effective to induce menstruation during each discontinuance period.

2. The method of claim 1, wherein the administration period is about four months.

3. The method of claim 1, wherein said female is administered a progestin selected from the group consisting of medroxyprogesterone, hydroxyprogesterone and progesterone.

4. The method of claim 1, wherein said SPRM is CDB-4124 (21-methoxy-17α-acetoxy-11β-(4-N,N-dimethylaminophenyl)-19-norpregna-4,9-diene-3,20-dione).

5. The method of claim 4, wherein the administration period is about four months.

6. The method of claim 1 wherein the progesterone antagonist is 17α-acetoxy-11β-(4-N,N-dimethylaminophenyl)-19-norpregna-4,9-dien-3,20-dione.

7. The method of claim 1, wherein the SPRM is orally administered.

* * * * *